United States Patent [19]

Sambale et al.

[11] Patent Number: 5,079,167

[45] Date of Patent: Jan. 7, 1992

[54] METHOD OF RACEMATE RESOLUTION

[75] Inventors: Clemens Sambale, Braunschweig; Maria-Regina Kula, Niederzier-Hambach; Werner Hummel, Titz; Karlheinz Drauz, Freigericht, all of Fed. Rep. of Germany

[73] Assignees: Gesellschaft fur Biotechnologische Forschung mbH (GBF), Brunswick; Degussa AG, Zweigniederlassung Wolfgang, Hanau, both of Fed. Rep. of Germany

[21] Appl. No.: 123,156

[22] PCT Filed: Feb. 25, 1987

[86] PCT No.: PCT/EP87/00107

§ 371 Date: Nov. 27, 1987

§ 102(e) Date: Nov. 27, 1987

[87] PCT Pub. No.: WO87/05329

PCT Pub. Date: Sep. 11, 1987

[30] Foreign Application Priority Data

Feb. 27, 1986 [DE] Fed. Rep. of Germany ....... 3606401

[51] Int. Cl.[5] .............................................. C12P 13/04
[52] U.S. Cl. .................................. 435/280; 435/106; 435/128
[58] Field of Search ........................................ 435/280

[56] References Cited

U.S. PATENT DOCUMENTS 4,202,943  5/1980  Suhara et al. ...................... 435/280

OTHER PUBLICATIONS

Baker et al–Am. J. Enol. Viliculture–vol. 27 No. 1 (1976) pp. 12–14.
Suhara et al–Chem. Abst. vol. 102 (1985) p. 20,930 f.
Sambale et al–Chem. Abst. vol. 107 (1987) p. 231, 994w.
Baker et al–Chem Abst. vol. 85 (1976) p. 29884g.

*Primary Examiner*—Sam Rosen
*Attorney, Agent, or Firm*—Kane, Dalsimer, Sullivan, Kurucz, Levy, Eisele and Richard

[57] ABSTRACT

The invention relates to a method for resolving carbamate racemates of amino acids or norephedrine by enzmatic resolution.

19 Claims, 1 Drawing Sheet

A3: x    A4: ◇    L8: △

L10: □    L12: ○    L18: *

METHOD OF RACEMATE RESOLUTION

BACKGROUND OF THE INVENTION

1. Field of the Invention

The invention relates to a method of racemate resolution.

2. Brief Description of the Prior Art

The constantly increasing need for amino acids leads to the existing sources being extended and optimized and furthermore to new ways of synthesis being discovered. In the chemical syntheses generally racemates are formed which must be separated in further steps into the antipodes.

SUMMARY OF THE INVENTION

According to the invention a method is provided for racemate resolution of amino acid derivatives which proceeds from an amino acid carbamate racemate and enzymatically resolves said racemate.

The advantage of using amino acid carbamates for preparing optically active amino acids is that in the synthesis of the starting compounds it is not necessary to start from the corresponding amino acids but that amino acid precursor (for example alpha-halogen carboxylic acid) can be converted directly to the carbamates.

The method according to the invention for racemate resolution can also be applied to the norephedrine carbamate racemate. Norephedrine acts as sympathomimetic.

In the method according to the invention for example methyl carbamates with the methoxycarbonyl group may be used.

Advantageously a water-soluble amino acid carbamate racemate and/or the racemate of a naturally occurring amino acid is used.

DETAILED DESCRIPTION OF THE PREFERRED EMBODIMENTS OF THE INVENTION

Figure 1:
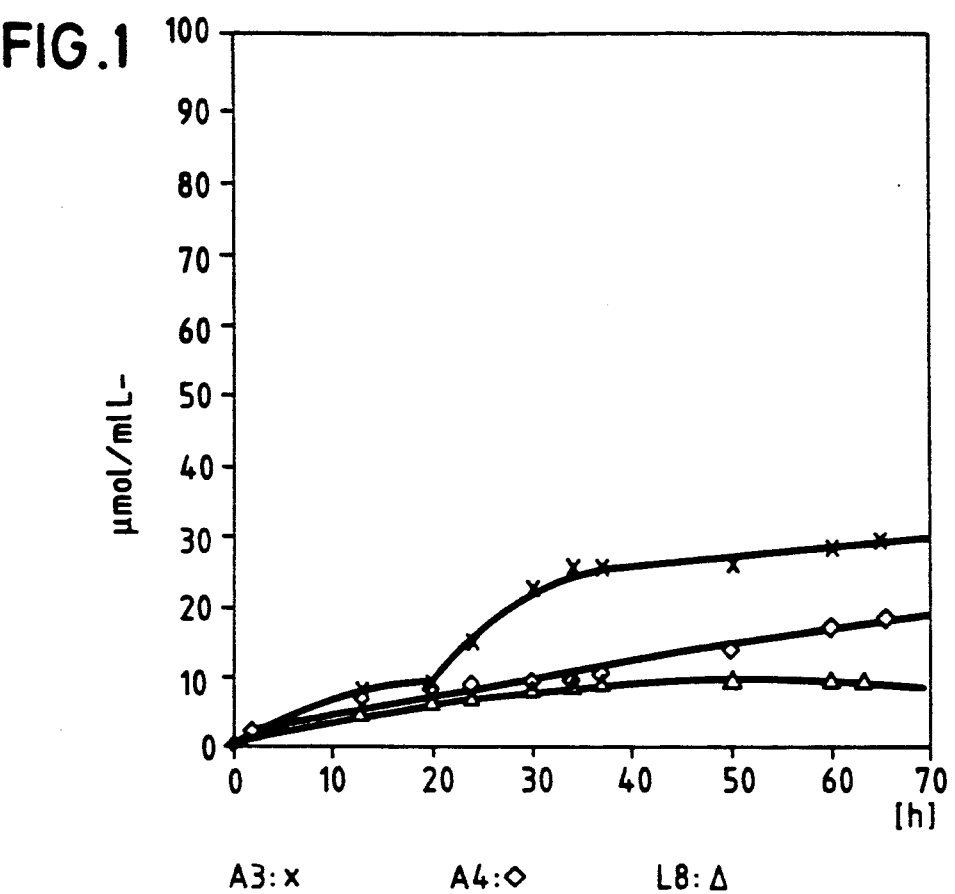

The method according to the invention may be carried out (a) with the aid of a microorganism which has an enzyme activity which hydrolytically resolves one of the enantiomers of an amino acid carbamate racemate or norephedrine carbamate racemate and which has been found in a test for said enzyme activity, or (b) with the aid of the enzyme activity of the microorganism according to (a).

In variant (b) the resolution may be carried out with the aid of the enzyme activity in the form of the culture medium of the microorganism according to variant (a), of the culture medium separated from the microorganism, an extract of the culture medium or an extract of the microorganism.

Suitable microorganisms can be obtained from soil samples. For the isolation for example soil samples may be used which have been treated with carbamates. It is easily conceivable that for example land which has been treated with carbamate pesticides such as Betanal or Unden, carbamate-decomposing microorganisms live which enjoy therein a selection advantage so that an enrichment of strains with the desired characteristics can occur.

In another embodiment the method according to the invention may also be carried out with the aid of an enzyme which hydrolytically resolves one of the enantiomers of an amino acid carbamate racemate or norephedrine carbamate racemate and which has been determined in a test for this enzyme activity.

Such enzymes can open up a wide area of new uses. Possible uses are conceivable in peptide synthesis where a mild splitting off of protective groups introduced, for example t-butyloxycarbonyl or benzoxycarbonyl groups is of great interest.

Finally, according to an embodiment of the method according to the invention the optically active amino acid, in particular L-amino acid, forming in the racemate resolution is isolated and/or the optically active carbamate of the amino acid, in particular D-amino acid, enantiomeric to the formed amino acid and further forming in the racemate resolution is resolved in a manner familiar to one skilled in the art and the enantiomeric amino acid recovered.

In the following examples, for instance the following enzymatic racemate resolution will be described:

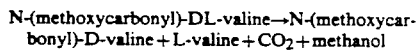

N-(methoxycarbonyl)-DL-valine→N-(methoxycarbonyl)-D-valine + L-valine + $CO_2$ + methanol Since the $CO_2$ is removed from the equilibrium the latter is constantly shifted to the right or downwards so that both enantiomers can be recovered with high purity.

Below the invention will be explained in detail with the aid of experimental methods and examples.

Execution of a screening with soil samples

One gram soil sample was incubated in 100 ml minimum medium (M2) containing a carbamate derivative as sole C and N source at 27° C. and 100 rpm in a rotary vibrator. After 48 h, with 1% (v/v) a further culture was inoculated into the same medium. For recovering single colonies a dilution series with sterile saline* was made. Aliquots are spread onto agar plates with the minimum medium (M2). The Petri dishes are incubated at 27° C. for 3-7 days.

Organisms which exhibited good growth were purified by dilution smear. The purified strains were transferred by inoculation in 100 ml liquid medium (M1) to 500 ml Erlenmeyer flasks having 2 baffles and grown at 27° C. in the rotary vibrator with 100 rpm. After 1-3 days the flask contents were centrifuged off. The sediment was suspended in 0.1 M potassium phosphate buffer pH 8.0. The cell splitting was done ultrasonically. Insoluble components were centrifuged off (30000 g, 4° C.). The supernatant was used directly for the enzyme test or first deep-frozen (−20° C.).

| Medium for screened strains (M1) | |
|---|---|
| Potassium dihydrogen phosphate | 0.80 g |
| Dipotassium hydrogen phosphate | 1.76 g |
| Yeast extract | 0.50 g |
| NaCl | 0.50 g |
| Glucose | 5.00 g |
| Amino acid carbamate derivative | 5.00 g |
| made up with dist. $H_2O$ | 1.00 l pH 7.0 |
| Medium for concentration of microorganisms from soil samples (M2) | |
| Potassium dihydrogen phosphate | 0.80 g |
| Dipotassium hydrogen phosphate | 1.76 g |
| Trace salt solution | 2.00 ml |
| Vitamin solution | 2.00 ml |

| -continued | |
|---|---|
| Amino acid carbamate derivative | 10.00 g |
| made up with dist. H$_2$O | 1.00 l pH 7.0 |
| Medium for fermentation (M4) | |
| Potassium dihydrogen phosphate | 0.80 g |
| Dipotassium hydrogen phosphate | 1.76 g |
| Methanol | 0.50% (v/v) |
| Yeast extract | 5,00 g |
| Malt extract | 5.00 g |
| NaCl | 3.00 g |
| made up with dist. H$_2$O | 1.00 l pH 7.00 |

Saline buffer:
8.5 g sodium chloride
0.3 g KH$_2$PO$_4$
0.6 g Na$_2$HPO$_4$
10 ml 1% gelatin (Merck)
990 ml H$_2$O

Culture Development

Shake Cultures

Shake cultures were grown at 30° C. in 500 ml Erylenmeyer flasks (two baffles) with 100 ml culture medium on a rotary vibrator (100 rpm). The inoculation was from a slant agar culture with an inoculating loop. After 48 h inoculation was carried out from this first initial culture with 1% (v/v) to a further initial culture. The latter served as initial culture for further test series in turn inoculated after 24 h with 3% (v/v) from the latter.

Culture Development in the Fermenter (10 l working volume)

The fermenter was sterilized one day prior to the inoculation. It was thus possible before the inoculation to ensure saturation of the culture medium with oxygen and constant temperature (30° C.±1° C.). The sterilization of the fermenter volume was in situ with hot steam for 30–60 min, 121° C., 1.2 bar, with a stirring speed of 100 rpm. The C sources were aseptically added to the fermenter initial charge 1–2 h prior to the seeding. For correcting the pH value 1 M KOH or 1 M H$_3$PO$_4$ was used. For the entire fermentation process usually constant aeration was carried out with 1 vvm (initial value) and stirring with 200 rpm.

Unless otherwise stated, the following parameters were maintained in the fermenters:
Speed: 200 rpm
Aeration: 1 vvm
Temperature: 30° C.
Nutrient solution: M4
pH: 7.0
Culture duration 40–80 hours
During the culture development the following values were continuously measured:
the oxygen partial pressure
methanol concentration in the exit air via an FID
oxygen volume concentration of the discharging reactor air (vol %)
carbon dioxide volume concentration of the discharging reactor air (vol %)
pH value
culture temperature
aeration rate
For further characterization of the culture development discontinuous samples were withdrawn via sterilizable valve and used for analyses.

Amino Acid Analyzer

The quantitative determination of the amino acids was in an amino acid analyzer or in the fluorimetric test
Amino acid analyzer: Biotronik LC 6000
Column: Biotronik DC-4A (Dionex)
Initial column: Biotronik DC-3
Reaction temperature T$_1$: 49° C., T$_2$: 63° C.
Detection: Biotronik photometer Bt 6620 570 nm; 440 nm
Analysis time: 110–140 min
Sample amount: 100 μl
Calibration solution: Calbiochem—Behring Corp. Amino Acid Calibration Standard Type H
With the fixedly set program the following retention times were obtained:

| | |
|---|---|
| lysine | 92.6 min |
| α-benzoxycarbonyl lysine | 83.2 min |
| ε-benzoxycarbonyl lysine | 82.6 min |
| α-acetyl lysine | 63.9 min |
| α-methoxycarbonyl lysine | 50.7 min |
| ε-methoxycarbonyl lysine | 48.6 min |
| methionine | 48.6 min |
| ε-ethoxycarbonyl L-lysine | 48.4 min |
| valine | 43.3 min |
| alanine | 40.4 min |
| ε-acetyl lysine | 36.3 min |

| Dilution buffer /pH 1.85 | 19.60 g Na citrate × 2 H$_2$O |
|---|---|
| | 16.5 ml HCl conc. |
| | 20.0 ml thioethanol (dist.) |
| | 0.1 ml caprylic acid |
| | made up to 5 l with dist. H$_2$O |
| Separating buffer: | |
| Buffer A: /pH 3.20 | 88.2 g Na citrate × 2 H$_2$O |
| | 55–60 ml HCl conc. |
| | 3.2 ml thiodiethanol (redistilled) |
| | 12.0 ml 25% Brij |
| | 1.0 ml phenol |
| | 75.0 ml ethylglycol monomethylether |
| | made up to 5 l with dist. H$_2$O |
| Buffer B: /pH 3.93 | 88.2 g Na citrate × 2 H$_2$O |
| | 29.0 g NaCl |
| | 43.0 ml HCl conc. |
| | 12.0 ml 25% Brij |
| | 1.0 ml phenol |
| | made up to 5 l with dist. H$_2$O |
| Buffer C: /pH 5.00 | 88.2 g Na citrate × 2 H$_2$O |
| | 29.0 g NaCl |
| | 5.0 ml HCl conc. |
| | 12.0 ml 25% Brij |
| | 1.0 ml phenol |
| | made up to 5 l with dist. H$_2$O |
| Buffer D: /pH 9.66 | 171.5 g Na citrate × 2 H$_2$O |
| | 15.5 g H$_3$BO$_3$ |
| | 1.5 g NaOH |
| | 12.0 ml 25% Brij |
| | made up to 5 l with dist. H$_2$O |
| Ninhydrin solution: | 3.0 l ethylenegylcol monomethylether M 859 |
| | 80.0 g ninhydrin p.A. |
| | 1.0 l 4M Na acetate buffer pH 5.51 |
| | 20.0 ml titanium III chloride solution 15% |

Fluorimetric Test

Reagents 0.2 M sodium borate buffer pH 9.2 Fluram acetone solution (20 mg/100 ml)

Aliquots of the amino acid solution (0.1 to 100 nmol/ml) to be determined were added to 2.25 ml sodium borate buffer.

With rapid shaking in a vortex mixer 0.75 ml of the Fluram acetone solution were added. Rapid addition and rapid mixing are essential to achieve an optimum result. The fluorescence was measured in a Perkin-Elmer LS-5 luminescence meter with a stimulation wavelength of 390 nm and an emission wavelength of 475 nm to 490 nm. The associated values were determined from a calibration curve.

Checking the Stereospecificity Polarimeter

The measurements were carried out on the Perkin-Elmer polarimeter type 241 at 436 nm and 25° C. Calibration series were made in the range of 0–300 mM with which it was possible to determine quantitatively the amino acid concentration.

Definitions:

$$\text{specific rotation } (\alpha) = \frac{a}{c \times l}$$

$$\text{optical purity } p = \frac{\alpha}{\alpha_{max}}$$

($\alpha$): specific rotation   $a$: rotation
$c$: concentration g/l   $l$: length (dm)

L-Amino Acid Oxidase Test

L-amino acid oxidase from Crotalus durissus was used to test for L-amino acids. The test was carried out according to the instructions of Boehringer Mannheim.

Solutions a) triethanol amine buffer 0.2 M, pH 7.6
b) o-dianisidine solution 23.2 mM
c) buffer amino acid solution +0.5 ml solution (b).
d) peroxidase (POD) 250 U/mg
e) enzyme solutions U/mg 1/100 or 1/50 or 1/20 diluted with distilled ice-cooled water.

| Reaction batch: | |
|---|---|
| Buffer solution (c) | 3.00 ml |
| POD suspension (d) | 0.01 ml |
| Enzyme solution (e) | 0.02 ml |

The reaction was carried out at 436 nm and 25° C. on a DU Beckmann spectral photometer.

A calibration series with L-alanine and L-valine showed a linear relationship in the region from 40 to 400 µM.

D-Amino Acid Oxidase Test

D-amino acid oxidase from pig kidney was used to test for D-amino acids. The test was carried out in accordance with the instructions of Boehringer Mannheim.

Solutions a) Tris buffer, 200 mM pH 8.3 gassified for 10 min with $O_2$.
b) NADH solution, 12 mM (10 mg NADH, Na salt/ml $H_2O$)
c) Catalase solution: about 260,000 U/ml diluted 1:100 in distilled water.
d) Lactate dehydrogenase (LDH) about 450 U/mg
e) Enzyme solutions, about 15 U/mg diluted 1/50, 1/20, 1/10 with ice-cold water.

A calibration series with D-alanine and D-valine showed a linear relationship from 10 to 350 µM. The detection limit was 5 µM D-amino acid.

| Reaction batch: | |
|---|---|
| Tris buffer (a) | 2.50 ml |
| Amino acid test solution | 0.50 ml |
| NADH solution (b) | 0.05 ml |
| Catalase solution (c) | 0.01 ml |
| LDH suspension (d) | 0.01 ml |
| Enzyme solution (e) | 0.01 ml |

The change of the light absorption at 340 nm was measured spectrophotometrically at 25° C.

Examples 1 to 42

In the search for microorganisms with enzymes hydrolyzing amino acid carbamates stereoselectively soil samples from different locations were used to enable isolation of the broadest possible spectrum of microorganisms.

The samples were taken on a farm and on land treated with the carbamate pesticides Betanal 32 and Unden 33.

The screening result did not show any preferable location. The microorganisms washed out of the soil were grown on N-(methoxycarbonyl)-DL-alanine, N-(methoxycarbonyl)-DL-valine or N-alpha-epsilon-(dimethoxycarbonyl)-DL-lysine in each case as single C and N source. On N-(methoxycarbonyl)-DL-valine appreciably less strains were found than on the other two amino acid carbamates.

Of 42 strains found, 35 strains showed the highest enzyme activity in the conversion of the substrate N-(methoxycarbonyl)-DL-alanine. The enzymatic hydrolysis of N-alpha-epsilon-(dimethoxycarbonyl)-DL-lysine can theoretically lead to four compounds, D or L-enantiomer of the N-epsilon-(methoxy-carbonyl)-lysine, the N-alpha-(methoxycarbonyl)-DL-lysine and the lysine.

All strains which exhibited activity in the conversion of N-alpha-epsilon-(dimethoxycarbonyl)-DL-lysine formed the product N-epsilon-(methoxycarbonyl) lysine, of which in some cases the L-enantiomer could be detected. In the case of 5 of the 42 strains the free amino acid lysine was also detected. The compound N-alpha-(methoxycarbonyl)-DL-lysine could not be detected in any of the cases. The enzymes thus attack preferably the alpha-position in the lysine dicarbamate. It is striking that all the wild type isolates investigated in detail exhibited the expected stereoselectivity in the hydrolysis of the racemic amino acid carbamates.

Figure 2:
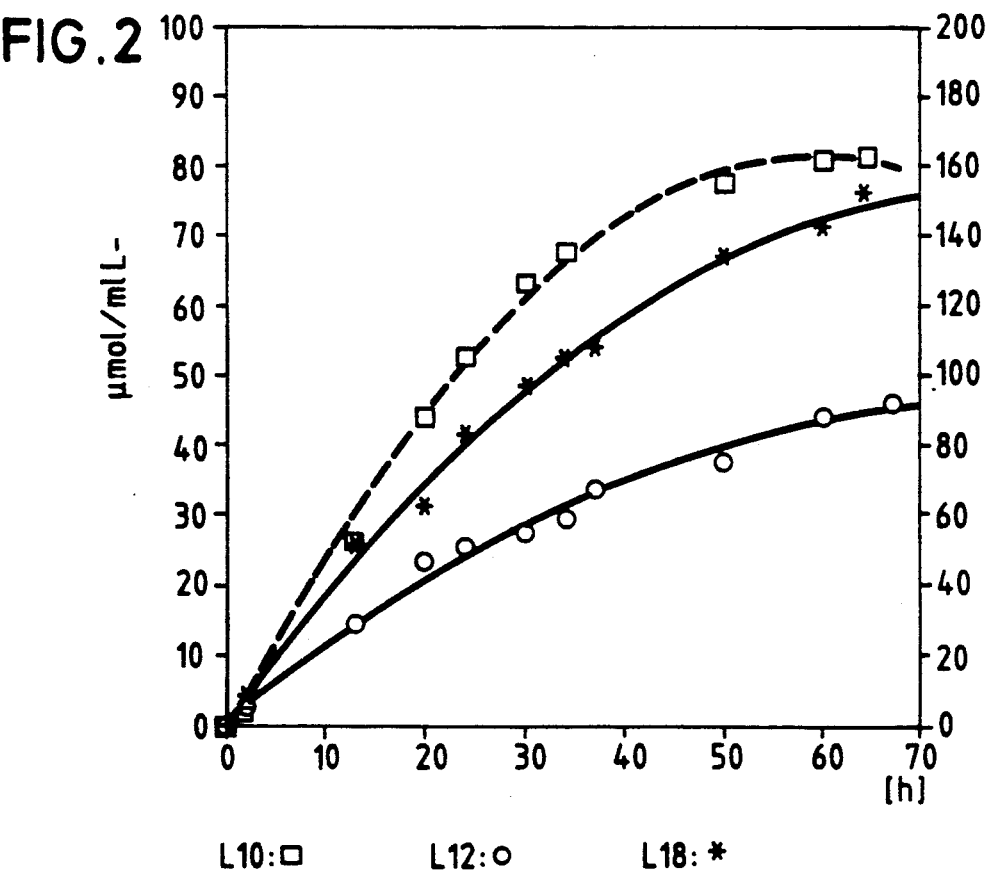

The results of the long-time reactions with 6 of the 42 strains found are shown in Table 1 and FIGS. 1 and 2.

TABLE 1

| | Long-time reaction of cell-free crude extract with the substrate N-(methoxycarbonyl)-DL-valine. | | | | | |
|---|---|---|---|---|---|---|
| | Protein | Substrate | Inc. | Product | | Yield |
| Strain | mg/ml | mmol/40 ml | time/h | mmol/40 ml | mg/40 ml | % |
| A4 | 1.2 | 7.0 | 65.0 | 1.18 | 138.2 | 33.71 |

TABLE 1-continued

| | Long-time reaction of cell-free crude extract with the substrate N-(methoxycarbonyl)-DL-valine. | | | | | |
|---|---|---|---|---|---|---|
| | Protein | Substrate | Inc. | Product | | Yield |
| Strain | mg/ml | mmol/40 ml | time/h | mmol/40 ml | mg/40 ml | % |
| A3 | 0.2 | 7.0 | 65.5 | 0.74 | 86.6 | 21.14 |
| L8 | 1.5 | 7.0 | 63.5 | 0.37 | 44.7 | 10.74 |
| L10 | 0.5 | 7.0 | 67.0 | 1.84 | 215.8 | 52.65 |
| L12 | 4.0 | 7.0 | 64.0 | 2.99 | 350.2 | 85.43 |
| L18 | 1.4 | 14.0 | 64.5 | 6.50 | 761.4 | 92.86 |

The stereospecificity of the biotransformation with the six microorganism strains was also proved by the fact that the compound N-(methoxycarbonyl)-D-valine was not converted. The activity path of strain A3 is striking. Since crude extracts were involved a number of factors, for example inhibitors, can influence the reaction path.

Examples 43 to 50

The hydrolytic conversion of the amino acid carbamates to amino acid, carbon dioxide and alcohol can be effected by enzymatic attack at the amide bond or ester bond. These considerations led to the question as to the extent which commercially available enzymes which cleave the ester and a amide bonds would accept amino acid carbamates as substrates. An esterase, three acetyl cholinesterases, a hydantoinase, a urease and two acylases were investigated.

Carboxylesterase (example 43) from pig liver did not show any reaction. Whereas the acetyl cholinesterase from eel (example 44) did not convert the amino acid carbamates enzyme activity was found for acetyl cholinesterase from bovine (example 45) and human (example 46) ethythrocytes. Only the L-amino acid carbamates were converted. The D-antipode used as substrate did not show any reaction.

The enzymes exhibited good stability. In incubation batches for a period of 150 hours linear substrate conversion was achieved. Hydantoinase from *Pseudomonas fluorescens* (example 47) did not exhibit any activity. Nor was any activity found for urease (example 48). The activity sought was also detected from fungus acylase (example 49) and the acylase from pig kidney (example 50).

Table 2 shows a comparison of the percentage conversion rate of acetyl and carbamate amino acids with kidney acylase. The reactions were L-specific.

TABLE 2

| Substrate specificity of amino acylase from pig kidney (with respect to alanine (100%)). | | | | |
|---|---|---|---|---|
| Acyl amino acids | | Amino acid carbamates | | |
| Amino acid | $-\underset{O}{\overset{\|}{C}}-R$ | | $-\underset{O}{\overset{\|}{C}}-OR$ | relative conversion rate |
| Alanine | chloroacetyl | 100 | methoxycarbonyl | 100 |
| | acetyl | 27 | ethoxycarbonyl | 89 |
| Valine | acetyl | 14.5 | methoxycarbonyl | 71 |
| | | | ethoxycarbonyl | 59 |

What is claimed is:

1. A method for resolving an amino acid carbamate racemate selected from the group consisting of a methyl carbamate of a DL-amino acid and an ethyl carbamate of a DL-amino acid, which comprises;
enzymatic resolution of the racemate selected with an enzyme which cleaves the amide or the ester bond, in the selected racemate whereby stereoselective hydrolysis resolves one of the enantiomers of the DL-amino acid carbamate racemate, whereby there is obtained an anantiomer of the DL-amino acid.

2. The method according to claim 1, wherein said carbamate racemate is a methyl carbamate.

3. The method according to claim 1 wherein the carbamate racemate is water soluble.

4. The method according to claim 1, wherein the amino acid carbamate racemate is a naturally occurring amino acid.

5. The method according to claim 1 wherein enzymatic resolution is carried out by a microorganism with an enzyme activity.

6. The method according to claim 5, wherein the resolution is carried out with the aid of the enzyme activity selected from the group consisting of a culture medium of the microorganism, a culture medium separated from the microorganism, an extract from the culture medium and an extract from the microorganism.

7. Method according to claim 1, when resolution is carried out enzymatically with the aid of a microorganism or the enzyme activity of a microorganism which has been isolated from a soil sample.

8. The method according to claim 7, wherein the soil sample has been treated with carbamates.

9. Method according to claim 1, wherein the method is carried out with the aid of an enzyme which hydrolytically resolves one of the enantiomers of an amino acid carbamate racemate and which has been determined in a test for said enzyme activity.

10. Method according to claim 1, wherein an optically active amino acid, is isolated.

11. The method of claim 10 wherein the optically active amino acid is a D-amino acid.

12. The method of claim 10 wherein the optically active amino acid is an L-amino acid.

13. A method for the resolution of a compound selected from the group consisting of racemic N-(methoxycarbonyl) norephedrine and racemic N-ethoxycarbonyl) norephedrine, which comprises; enzymatic resolution of the racemate selected with an enzyme which cleaves the amide bond in the selected compound, whereby stereoselective hydrolysis resolves one of the enantiomers oft he racemate and there is obtained an enantiomer of the norephedrine.

14. A method of claim 13 wherein the compound selected is racemic N-(methoxycarbonyl)norephedrine.

15. A method of claim 13 wherein the compound selected is racemic N-(ethoxycarbonyl)norephedrine.

16. A method of claim 13 wherein enzymatic resolution is carried out with a microorganism with an enzyme activity which hydrolytically resolves one enantiomer.

17. A method of claim 13 wherein the enzymatic resolution is carried out with the aid of the enzyme activity selected from the group consisting of a culture medium of a microorganism, a culture medium separated from said microorganism, an extract from said culture medium and an extract from said microorganism.

18. A method of claim 13 wherein the resolution is carried out enzymatically with the aid of a microorganism or the enzyme activity of a microorganism which has been isolated from a solid sample.

19. A method of claim 18 wherein the said sample has been treated with a carbamate.

* * * * *